(12) United States Patent
Silber

(10) Patent No.: US 7,856,261 B2
(45) Date of Patent: Dec. 21, 2010

(54) CABLE WITH SPACER FOR POSITIONING MULTIPLE MEDICAL SENSORS

(75) Inventor: Daniel A. Silber, Lexington, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 717 days.

(21) Appl. No.: 11/720,896

(22) PCT Filed: Dec. 5, 2005

(86) PCT No.: PCT/IB2005/054064

§ 371 (c)(1),
(2), (4) Date: Jun. 5, 2007

(87) PCT Pub. No.: WO2006/064398

PCT Pub. Date: Jun. 22, 2006

(65) Prior Publication Data

US 2009/0227858 A1     Sep. 10, 2009

Related U.S. Application Data

(60) Provisional application No. 60/635,646, filed on Dec. 13, 2004.

(51) Int. Cl.
*A61B 5/04* (2006.01)
(52) U.S. Cl. .................................................. 600/509

(58) Field of Classification Search .......... 600/508–523
See application file for complete search history.

(56) References Cited

U.S. PATENT DOCUMENTS

| RE30,101 | E | 9/1979 | Kubicek et al. | |
|---|---|---|---|---|
| 4,957,109 | A * | 9/1990 | Groeger et al. | 600/391 |
| 5,042,481 | A | 8/1991 | Suzuki et al. | |
| 5,231,990 | A * | 8/1993 | Gauglitz | 600/510 |
| 6,066,093 | A | 5/2000 | Kelly et al. | |
| 6,561,986 | B2 | 5/2003 | Baura et al. | |
| 6,602,201 | B1 | 8/2003 | Hepp et al. | |
| 6,636,754 | B1 | 10/2003 | Baura et al. | |
| 7,197,357 | B2 * | 3/2007 | Istvan et al. | 600/509 |

FOREIGN PATENT DOCUMENTS

WO     2004084985 A1    10/2004

* cited by examiner

*Primary Examiner*—Carl H Layno
*Assistant Examiner*—Brian T Gedeon

(57) ABSTRACT

A subject monitoring apparatus is provided. The apparatus includes a drive unit (10); a sensor unit (50); and a plurality of cable end units (500) for providing electrical connection between electrodes disposed on a subject and cables passing from the cable end units to the drive and sensor units. Each cable end unit includes first and second connectors (340, 380), and a spacer (400) which substantially maintains a pre-determined distance (L) between the first and second connectors.

18 Claims, 4 Drawing Sheets

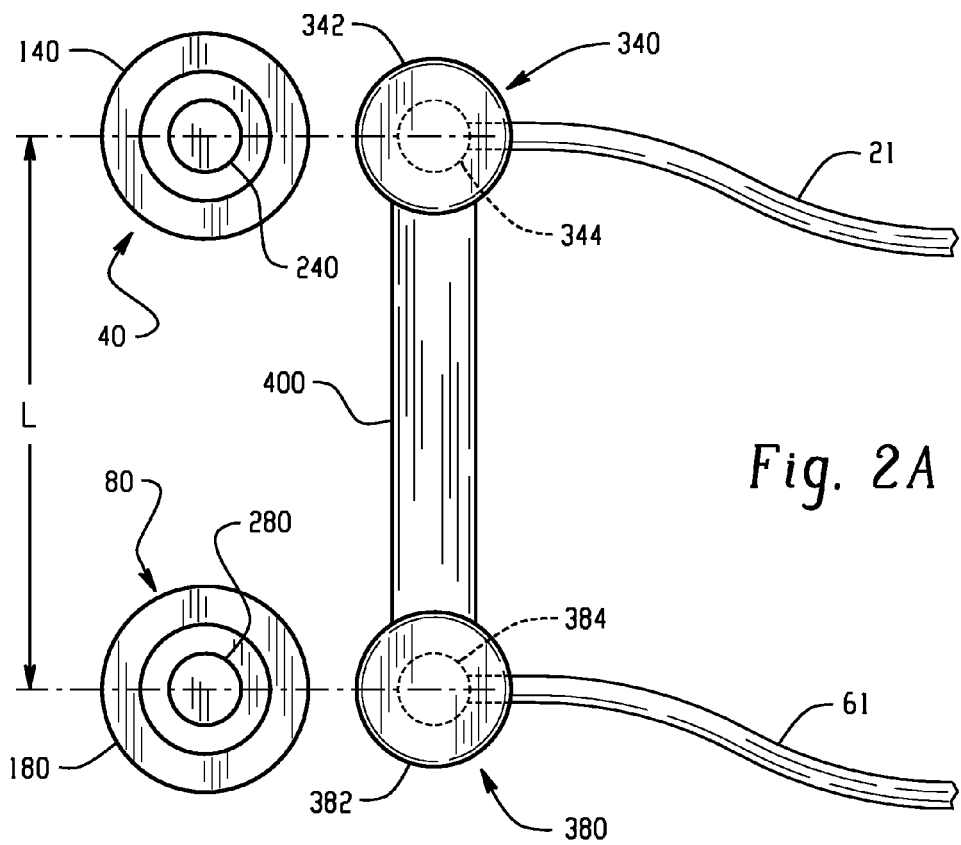
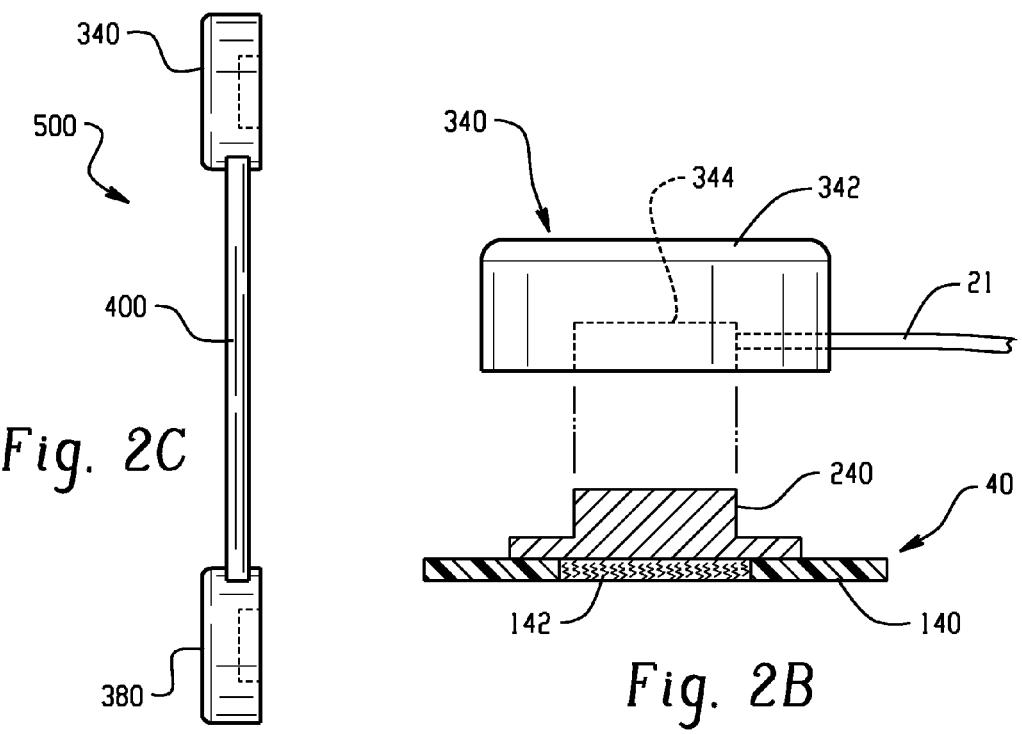

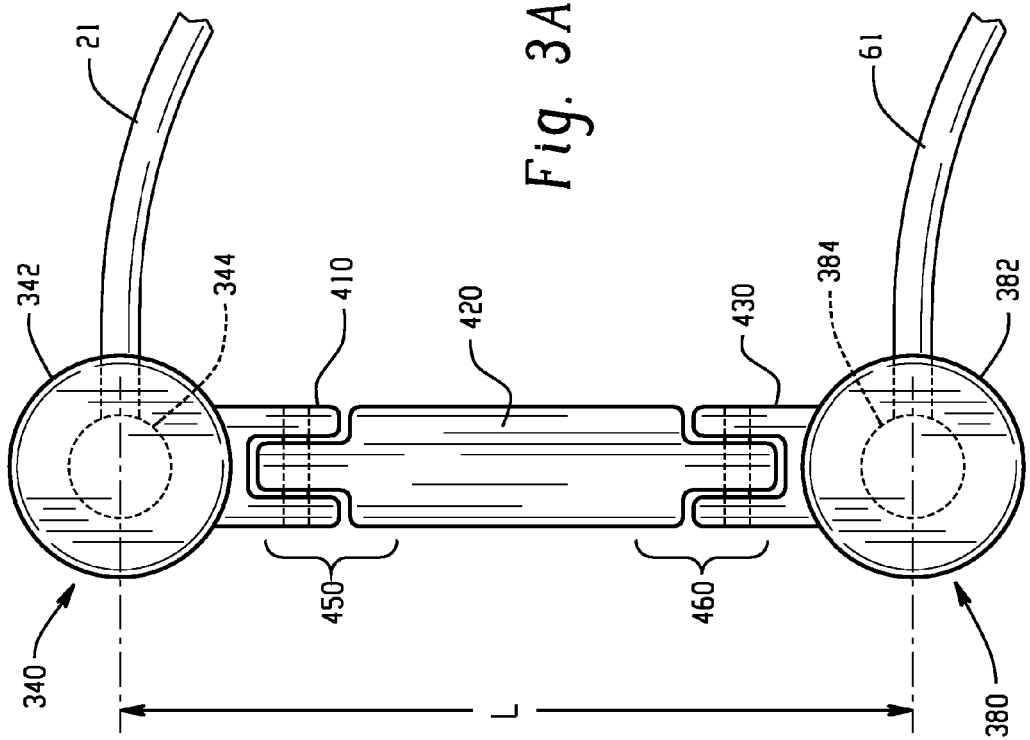
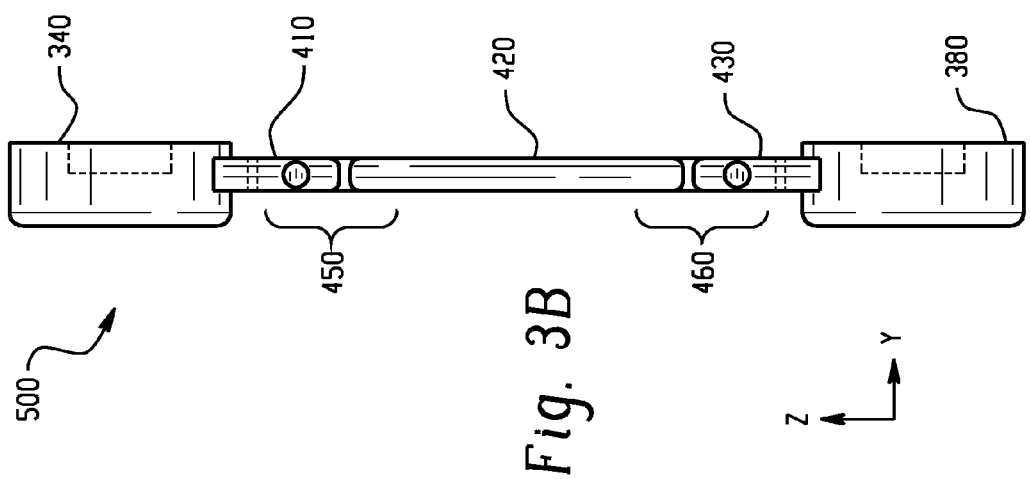

CABLE WITH SPACER FOR POSITIONING MULTIPLE MEDICAL SENSORS

CROSS REFERENCE TO RELATED APPLICATIONS

This application claims the benefit of U.S. provisional application Ser. No. 60/635,646 filed Dec. 13, 2004, which is incorporated herein by reference.

The following relates to patient monitoring. It finds particular application in impedance cardiography and will be described with particular reference thereto.

The study of the performance and properties of the cardiovascular system of a living subject can be useful for diagnosing and assessing any number of conditions or diseases within the subject. The performance of the cardiovascular system, including the heart, has characteristically been measured in terms of several output parameters, including the stroke volume and cardiac output of the heart.

Impedance cardiography (ICG), also known as thoracic electrical bioimpedance (TEB), is a technology that measures changes in thoracic impedance and relates them to such stroke volume and cardiac output parameters of the heart. In this manner, ICG is used to track volumetric changes such as those occurring during the cardiac cycle. These measurements, which are gathered noninvasively and continuously, have become more sophisticated and more accurate with the development of data signal processing and improved mathematical algorithms.

More strictly speaking, impedance cardiography is used to measure the stroke volume of the heart and heart rate. As shown in Eq. (1), when the stroke volume is multiplied by heart rate, cardiac output (CO) is obtained.

$$CO = \text{Stroke Volume} \times \text{Heart Rate} \quad (1)$$

During impedance cardiography, a constant alternating current, with a frequency such as 70 kHz is applied across the thorax. The resulting voltage is used to calculate impedance. The calculated impedance is then used to calculate stroke volume in accordance with known calculations.

A basic method of correlating thoracic, or chest cavity, impedance, $Z_T(t)$, with stroke volume generally includes modeling the thoracic impedance $Z_T(t)$ as a constant impedance, $Z_o$ and a time-varying impedance, $\Delta Z(t)$. The time-varying impedance is measured by way of an impedance waveform derived from electrodes placed on various locations of the subject's thorax; changes in the impedance over time can then be related to the change in fluid volume (i.e., stroke volume), and ultimately cardiac output via Equation (1) above.

The method described above used continuous electrode bands around the neck and lower thorax. In an effort to increase comfort and utility, standard ECG electrodes were subsequently used. With ECG electrodes, proper diagnosis depended on the user's knowledge and care in placing these electrodes properly.

Despite their general utility, the previous impedance cardiography techniques suffered from certain disabilities. First, the distance (and orientation) between the terminals of the electrodes which are placed on the skin of the subject can be variable; this variability can introduce error into the impedance measurements. Specifically, individual electrodes which typically include a button snap-type connector, compliant substrate, and gel electrolyte, are affixed to the skin of the subject at locations determined by the user. Since there was no direct physical coupling between the individual electrodes, their placement has been somewhat arbitrary, both with respect to the subject and with respect to each other. Hence, two measurements of the same subject by the same user may produce different results, dependent at least in part on the user's choice of placement location for the electrodes. It has further been shown that with respect to impedance cardiography measurements, certain values of electrode spacing yield better results than other values.

In light of the foregoing, recent ICG electrodes have included two electrodes mounted a given distance, such as 5 cm, apart on a common substrate. These electrode pairs can be convenient, simple and reliable. However, due to the manufacturing requirements associated with such electrode pairs, the pairs can be more costly than the cost associated with using individual electrodes, as in the past. This fact, combined with the disposable nature of the electrodes, leads to undesirable costs of sensors used for ICG monitoring. A further drawback to these electrode pairs is that they are not always readily available for use.

Additionally, as the subject moves, contorts, and/or breathes during ICG protocols, the relative orientation and position of the individual electrodes may vary. Electrodes may also be displaced laterally to a different location on the skin through subject movement, tension on the electrical leads connected to the electrodes, or even incidental contact. This so-called "motion artifact" can also reflect itself as reduced accuracy of the cardiac output measurements obtained using the impedance cardiography device.

Based on the foregoing, there is a need for an improved apparatus and method for measuring cardiac output in a subject. The present invention contemplates an improved apparatus and method that overcomes the aforementioned limitations and others.

In accordance with one embodiment of the invention, a subject monitoring apparatus is provided. The apparatus includes a drive unit and a sensor unit. The apparatus also includes a plurality of cable end units for providing electrical connection between electrodes disposed on a subject and cables passing from the cable end units to the drive and sensor units. Each cable end unit includes first and second connectors, and a spacer which substantially maintains a pre-determined distance between the first and second connectors.

In accordance with another embodiment of the invention, a main cable is provided for use with subject monitors. The main cable includes first and second cable branches and a cable end unit disposed at terminal ends of the first and second cable branches. The cable end unit includes first and second connectors and a spacer which spaces the first and second connectors apart from each other substantially at a pre-determined distance.

In accordance with another embodiment of the invention, a method of monitoring a subject is provided. The method includes providing a drive signal to the subject and receiving a sense signal from the subject, the sense signal being related to the drive signal as a function of characteristics of the subject. The drive and sense signals are provided to and received from the subject via a plurality of cable end units for providing electrical connection between electrodes disposed on the subject and cables passing from the cable end units to drive and sensor units. Each cable end unit includes first and second connectors and a spacer which substantially maintains a pre-determined distance between the first and second connectors.

On advantage of an embodiment of the invention is that the use of electrodes fabricated in pairs is not necessary.

Another advantage of an embodiment of the invention is that use of standard electrocardiograph electrodes is facilitated.

Another advantage of an embodiment of the invention is that placing electrodes at a desired inter-electrode spacing is facilitated.

Another advantage of an embodiment of the invention is that motion of the electrodes can be accommodated while substantially maintaining desired inter-electrode spacing.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

FIG. 2A shows a top view of an impedance cardiograph cable with a spacer and a pair of electrodes.

FIG. 2B shows a cross-sectional view of an electrode and a connector.

FIG. 2C shows an end view of a cable end unit.

FIG. 3A shows an illustration of a spacer having two pivot joints.

FIG. 3B shows an end view of a cable end unit having two joints in its spacer.

Figure 1:
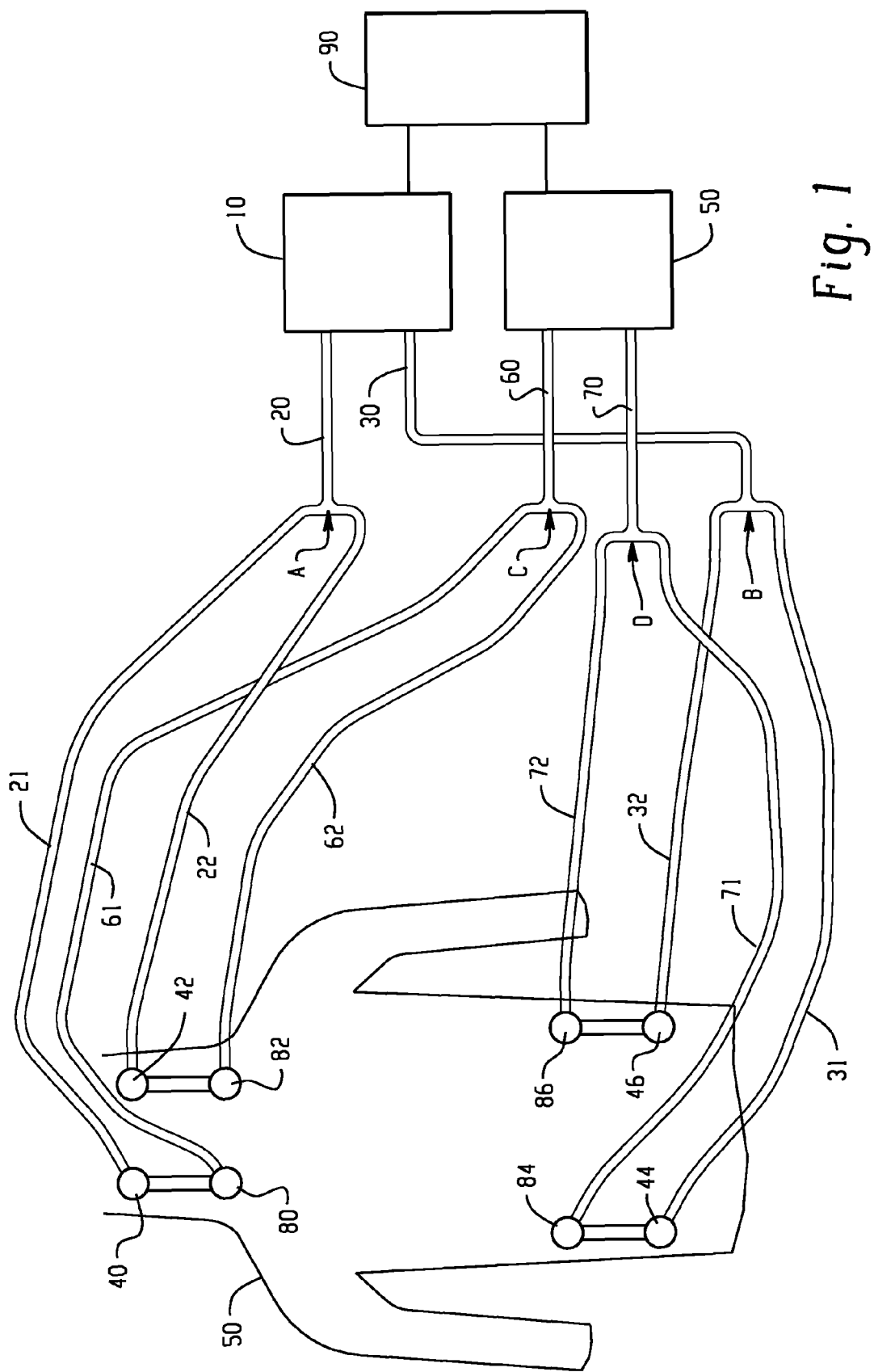
FIG. 1 shows a diagrammatic illustration of an impedance cardiography system.

With reference to FIG. 1, an embodiment of an impedance cardiography (ICG) system is shown. The ICG system includes a drive unit 10, first and second drive cables 20, 30 and first, second, third, and fourth drive electrodes 40, 42, 44, 46. The first and second drive electrodes 40, 42 are positioned in approximately equal superior/inferior positions on the right and left sides, respectively, of the neck of a subject 50 and are electrically connected to the drive unit 10 via the first drive cable 20. More specifically, the first drive cable 20 is divided into two branches at point A. The first branch 21 of the first drive cable is connected to the first drive electrode 40 and the second branch 22 of the first drive cable is connected to the second drive electrode 42.

The third and fourth drive electrodes 44, 46 are positioned in approximately equal superior/inferior positions on the right and left sides, respectively, of the thorax of the subject 50 and are electrically connected to the drive unit 10 via the second drive cable 30. More specifically, the second drive cable 30 is divided into two branches at point B. The first branch 31 of the second drive cable is connected to the third drive electrode 44 and the second branch 32 of the second drive cable is connected to the fourth drive electrode 46.

The ICG system also includes a sensor unit 50, first and second sensor cables 60, 70 and first, second, third, and fourth sensor electrodes 80, 82, 84, 86. The first and second sensor electrodes 80, 82 are positioned in approximately equal superior/inferior positions on the right and left sides, respectively, of the neck of a subject 50 and are electrically connected to the sensor unit 50 via the first sensor cable 60. With respect to the first and second drive electrodes 40, 42, the first and second sensor electrodes 80, 82 are positioned a given distance L in an inferior direction. Further, the first sensor cable 60 is divided into two branches at point C. The first branch 61 of the first sensor cable is connected to the first sensor electrode 80 and the second branch 62 of the first sensor cable is connected to the second sensor electrode 82.

The third and fourth sensor electrodes 84, 86 are positioned in approximately equal superior/inferior positions on the right and left sides, respectively, of the thorax of the subject 50 (approximately at the height of the xiphoid process) and are electrically connected to the sensor unit 50 via the second drive cable 70. With respect to the third and fourth drive electrodes 44, 46, the third and fourth sensor electrodes 84, 86 are positioned a given distance L (See FIG. 2A) in a superior direction. Further, the second drive cable 70 is divided into two branches at point D. The first branch 71 of the second sensor cable is connected to the third sensor electrode 84 and the second branch 72 of the second sensor cable is connected to the fourth sensor electrode 86.

While FIG. 1 shows various drive and sensor cables, it is to be understood that the illustrated cables can be packaged into a main cable while keeping the illustrated cables electrically isolated.

The drive unit and sensor unit are connected to a processing unit 90 which processes signals received from the drive and sensor units.

Turning to FIGS. 2A-2C, the pair of electrodes 40, 80 disposed on the right side of the subject's neck is shown. In the embodiment shown, the first drive electrode 40 can be an electrocardiograph (ECG) electrode. The electrode includes a base portion 140 which includes a flexible substrate and adhesive so that the electrode can be attached to the skin of the subject. The electrode also includes gel electrolyte 142 to facilitate electrical connection between the subject and the ICG system. The electrode also includes a male snap portion 240 which protrudes from the base portion 140 as shown in FIG. 2B. Similarly, the first sensor electrode 80 can be an ECG electrode which includes a base portion 180, gel electrolyte, and a male snap portion 280 which protrudes from the base portion 180.

Also shown are terminal ends of the first branch of the first drive cable 21 and the first branch of the first sensor cable 61. In the embodiment shown, the terminal end of the first branch of the first drive cable 21 includes a snap-type connector 340. The snap-type connector includes a housing 342 and a female snap portion 344 disposed within the housing. In operation the male and female snap portions 240, 344 are joined, or snapped together, to form an electrical contact between the drive electrode 40 and the first branch of the first drive cable 21.

Similarly, the terminal end of the first branch of the first sensor cable 61 includes a snap-type connector 380. The snap-type connector includes a housing 382 and a female snap portion 384 disposed within the housing. In operation the male and female snap portions 280, 384 are joined, or snapped together, to form an electrical contact between the sensor electrode 80 and the first branch of the first sensor cable 61.

In the embodiment shown in FIG. 2A, a cable spacer 400 connects the snap-type connectors 340, 380. The cable spacer 400 and connectors 340, 380 form a cable end unit 500. In one embodiment, the cable spacer and housings 342, 382 of the connectors are of unitary construction. In another embodiment, the cable spacer and housings are modular units which are fastened together by a molded plastic bar.

Continuing with FIG. 2A, the cable end unit is fabricated so that the centers of the snap-type connectors 340, 380 are spaced from each other by pre-determined distance L. In one embodiment, the pre-determined distance L is 50 millimeters.

In one embodiment, the end unit 500 can flex in response to the contour of subject as well as to motion of the subject yet still substantially maintain the spacing L between the centers of the connectors. In the embodiment shown in FIG. 2A, cable spacer 400 can be made of a semi-rigid material such as polyvinyl-chloride (PVC) or similar plastic which allows such flexion.

In the embodiment shown in FIGS. 3A-3B, the cable spacer 400 includes first, second, and third links 410, 420, 430 which are joined together at first and second joints 450, 460. In this embodiment, the first and second joints are hinge joints which allow flexion primarily about the x-axis as shown in FIG. 3B. Such an embodiment accommodates motion of the subject while substantially maintaining the spacing L between the electrodes.

Figure 4A:
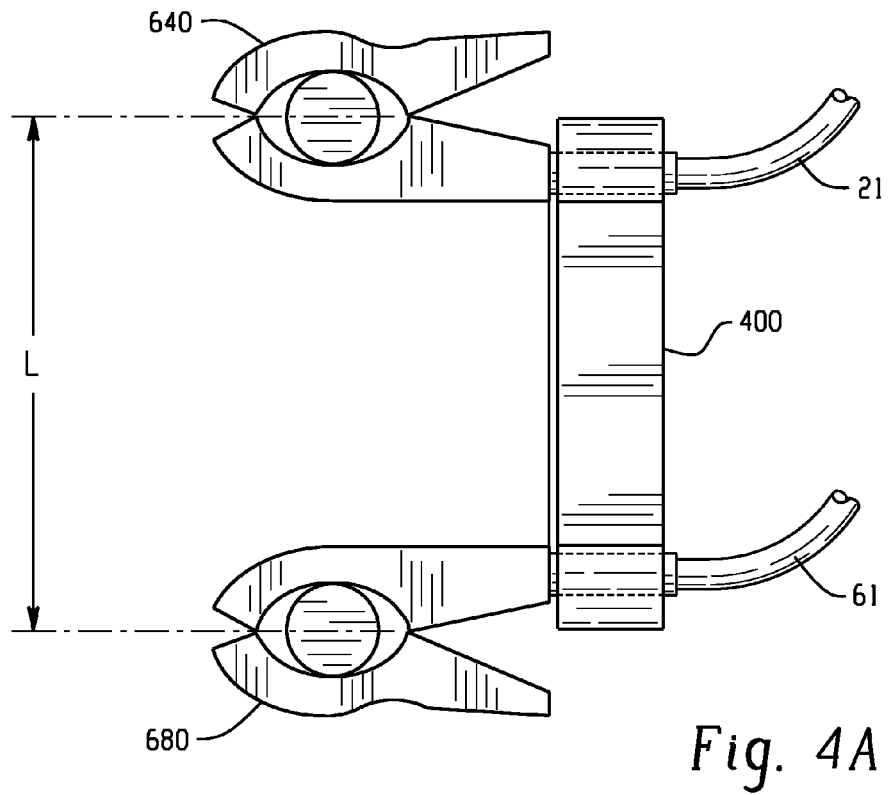
FIG. 4A shows an illustration of grabber terminals with a spacer.
Figure 4B:
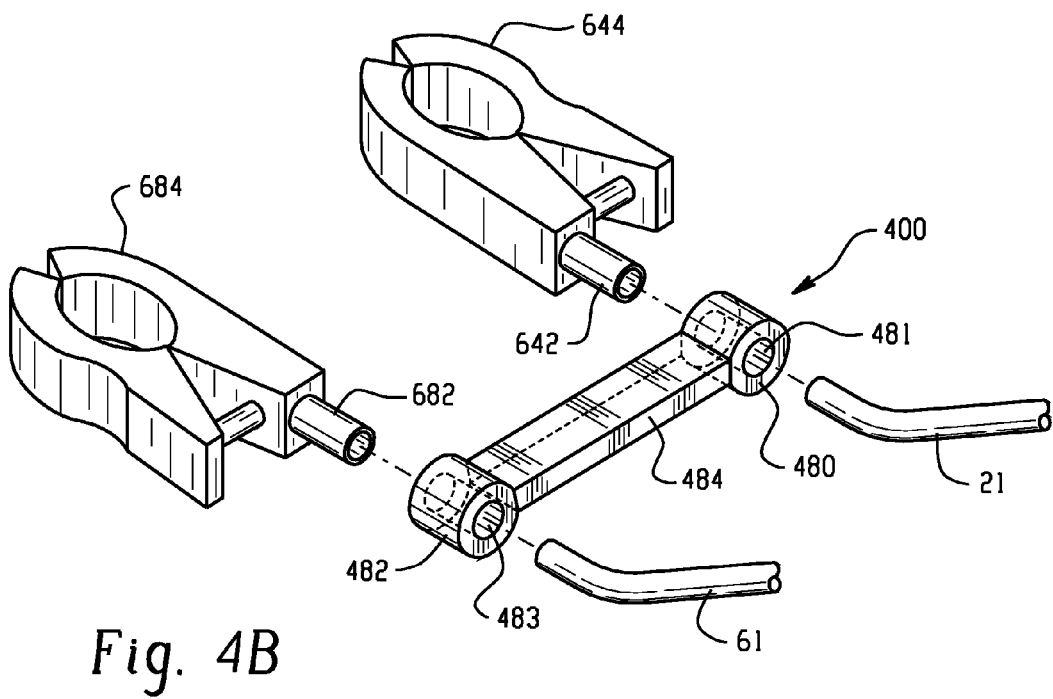
FIG. 4B shows a perspective illustration of grabber terminals with a spacer.

In the embodiment shown in FIGS. 4A and 4B, the terminal end of the first branch of the first drive cable 21 includes a grabber-type connector 640. The grabber-type connector includes a base portion 642 and a grabbing portion 644 connected to the base portion 642. In operation the grabbing portion is a spring-loaded device which holds the male snap portion 240 of the drive electrode 40 to form an electrical contact between the electrode 40 and the first branch of the first drive cable 21.

Continuing with the embodiment shown in FIGS. 4A and 4B, the terminal end of the first branch of the first sensor cable 61 includes a grabber-type connector 680. The grabber-type connector includes a base portion 682 and a grabbing portion 684 connected to the base portion 682. In operation the grabbing portion is a spring-loaded holding device which grabs the male snap portion 280 (FIG. 2A) of the sensor electrode 80 to form an electrical contact between the electrode 80 and the first branch of the first sensor cable 61.

In the embodiment shown in FIGS. 4A and 4B, the cable spacer 400 connects the grabber-type connectors 640, 680. The cable spacer 400 and connectors 640, 680 form the cable end unit 500. In one embodiment, shown in FIG. 4B the cable spacer includes first and second end portions 480, 482 which are bridged by a bridge member 484. Here, the cable spacer may be of unitary or modular construction. In this embodiment, the end portions include receiving passages 481, 483 for receiving the base portions of the grabber-type connectors.

In the embodiment shown, the base portions and the receiving passages are cylindrical and are sized to allow a fit between the base portions and the receiving passages. The fit between the base portions and the receiving passages can be a secure fit, or it may allow rotation of the base portions within the receiving passages while still maintaining the base portions within the receiving passages.

As discussed above, the cable spacer can be fabricated from material which allows flexion of the spacer or of various links and joints to allow flexion of the spacer.

While the foregoing description has been directed to the pair of electrodes on the right side of the subject's neck, it is to be understood that the other three pairs of electrodes disposed on the subject and their associated cables and connections can be described analogously.

It is also to be understood that the spacing L between electrodes can be made for other applications such as ECG, neurostimulation, electromyography, and the like.

In operation according to one embodiment of the invention, a cable with spacer(s) having desired inter-electrode spacing is selected. Electrodes are then connected to the connectors at the terminal ends of the cable branches. Once the electrodes have been attached to the cables, the electrodes are placed on the subject as shown in FIG. 1.

The drive unit 10 then provides, for example, a drive voltage or current, via the drive cables to the drive electrodes 40, 42, 44, 46. In one embodiment, a constant alternating current, with a frequency such as 70 kHz is applied to the drive electrodes. A resulting voltage is then measured using the sensor electrodes 80, 82, 84, 86. The voltage signals are taken from the sensors via respective sensor cables to the sensor unit 50.

Information related to the drive signal is sent from the drive unit to the processing unit 90. Also, the measured, or sensed, signals are sent from the sensor unit to the processing unit. The processing unit then uses the drive signal information and the received signals to calculate impedance. The calculated impedance is then used to calculate stroke volume, and cardiac output, in accordance with known calculations.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A subject monitoring apparatus comprising:
a drive unit;
a sensor unit;
a plurality of cable end units for providing electrical connection between electrodes disposed on a subject and cables passing from the cable end units to the drive and sensor units, each cable end unit comprising:
first and second connectors; and
a spacer which substantially maintains a pre-determined distance between the first and second connectors, said spacer comprising a plurality of links and a plurality of joints which join the links.

2. A subject monitoring apparatus as set forth in claim 1 wherein:
the first connector is disposed at a terminal end of a drive cable; and
the second connector is disposed at a terminal end of a sensor cable.

3. A subject monitoring apparatus as set forth in claim 2 wherein:
the first and second connectors have respective first and second housings and the first and second housings and the spacer are of unitary construction.

4. A subject monitoring apparatus as set forth in claim 2 wherein:
the spacer is flexible in a direction which accommodates shape and/or movement of the subject.

5. A subject monitoring apparatus as set forth in claim 2 wherein:
the electrodes include individually fabricated ECG electrodes.

6. A subject monitoring apparatus as set forth in claim 5 wherein:
each electrode includes a male snap portion which protrudes from a base portion; and
each connector includes one of a female snap portion and a grabber, for making connection with the male snap portion.

7. A subject monitoring apparatus as set forth in claim 1 wherein:
the joints include hinge joints.

8. An apparatus for electrically connecting a subject monitor with a subject, the apparatus comprising:
one or more cables including first and second cable branches having first and second terminal ends with respective first and second connectors wherein each connector is adapted to mechanically connect with an electrode secured to a subject to form electrical contact between the electrode and the respective cable branch; and a spacer disposed between the first and second terminal ends which maintains the first and second connectors spaced apart from each other substantially at a pre-determined distance, said spacer comprising a plurality of links and a plurality of joints which join the links.

9. An apparatus as set forth in claim 8 wherein:
the spacer is flexible.

10. An apparatus as set forth in claim 8 wherein:
the first cable branch is a drive branch of an impedance cardiography subject monitor; and
the second cable branch is a sensor branch of the impedance cardiography subject monitor.

11. A main cable for use with subject monitors, the cable comprising:
a plurality of first and second cable branches;
a plurality of cable end units disposed at terminal ends of the first and second cable branches;
the cable end unit comprising:
first and second connectors; and
a spacer which spaces the first and second connectors apart from each other substantially at a pre-determined distance, wherein the spacer is flexible and includes a plurality of links joined together by a plurality of hinge joints.

12. A method of monitoring a subject comprising:
providing a drive signal to the subject; and
receiving a sense signal from the subject, said sense signal being related to the drive signal as a function of characteristics of the subject, wherein:
the drive and sense signals are provided to and received from the subject via a plurality of cable end units for providing electrical connection between electrodes disposed on the subject and cables passing from the cable end units to drive and sensor units, each cable end unit comprising:
first and second connectors;
a spacer which substantially maintains a pre-determined distance between the first and second connectors; and
connecting the electrodes with the first and second connectors of the cable end unit that further includes the spacer which substantially maintains the pre-determined distance between the first and second connectors; and
after connecting the electrodes with the first and second connectors, placing the electrodes on the subject wherein the spacer substantially maintains the pre-determined distance between the first and second connectors during the placing.

13. A method of monitoring a subject as set forth in claim 12 wherein:
the first connector is disposed at a terminal end of a drive cable; and
the second connector is disposed at a terminal end of a sensor cable.

14. A method of monitoring a subject as set forth in claim 13 wherein:
the first and second connectors have respective first and second housings and the first and second housings and the spacer are of unitary construction.

15. A method of monitoring a subject as set forth in claim 13 wherein:
the spacer is flexible in a direction which accommodates shape and movement of the subject.

16. A method of monitoring a subject as set forth in claim 15 wherein:
the spacer includes a plurality of links and a plurality of joints which join the links.

17. A method of monitoring a subject as set forth in claim 16 wherein:
the joints include hinge joints.

18. A method of monitoring a subject as set forth in claim 13 wherein:
the electrodes include individually fabricated ECG electrodes.

* * * * *